United States Patent [19]

Greene et al.

[11] Patent Number: 4,643,197

[45] Date of Patent: Feb. 17, 1987

[54] SUCTION COLLECTION AND DRAINAGE APPARATUS

[75] Inventors: Franklin R. Greene, Flushing; Arthur L. Zimmet, Centerport; Jerome D. Waye, New York; Edward A. Petix, Syosset, all of N.Y.

[73] Assignee: E-Z-Em, Inc., Westbury, N.Y.

[21] Appl. No.: 733,214

[22] Filed: May 10, 1985

[51] Int. Cl.[4] .......................... A61B 5/00; A61M 1/00
[52] U.S. Cl. .................... 128/762; 604/319; 73/863.23
[58] Field of Search ............... 604/317–320; 128/760, 762, 766, 771; 73/863.23, 863.25, 863.45, 863.52, 863.56, 863.61, 863.82; 137/205, 73, 547; 210/247, 927, 416.1; 119/14.14, 14.32, 14.33, 14.34, 14.43

[56] References Cited

U.S. PATENT DOCUMENTS

| | | | |
|---|---|---|---|
| 2,784,717 | 3/1957 | Thompson | 604/319 |
| 3,929,133 | 12/1975 | Ragab | 604/319 |
| 3,982,538 | 9/1976 | Sharpe | 604/320 |
| 4,190,020 | 2/1980 | Tamás et al. | 119/14.14 |
| 4,384,580 | 5/1983 | Leviton | 604/319 |
| 4,385,590 | 5/1983 | Mortensen | 119/14.14 |
| 4,430,084 | 2/1984 | Deaton | 604/49 |

Primary Examiner—C. Fred Rosenbaum
Assistant Examiner—J. L. Kruter
Attorney, Agent, or Firm—McAulay, Fields, Fisher, Goldstein & Nissen

[57] ABSTRACT

The disclosure is directed to a suction collection and drainage apparatus which comprises a fluid collection container and a separate tissue specimen trap container. The collection container is connected, by a tube, to a source of suction. Another tube serves to connect the collection container and the trap container together to provide fluid communication therebetween. Still another tube serves to connect the trap container to an endoscope to permit collection of tissue specimens aspirated from the patient and transmitted to the trap container. A filter is supported within the trap container and is formed having a plurality of traps and a plurality of enlarged openings spaced around the filter. The filter is movable relative to the inlet of the tube between a first position wherein a selected one of the traps is positioned to receive and collect the tissue specimen and a second position wherein a selected one of the openings is positioned to permit passage therethrough of body fluids when suction is applied to the apparatus.

20 Claims, 8 Drawing Figures

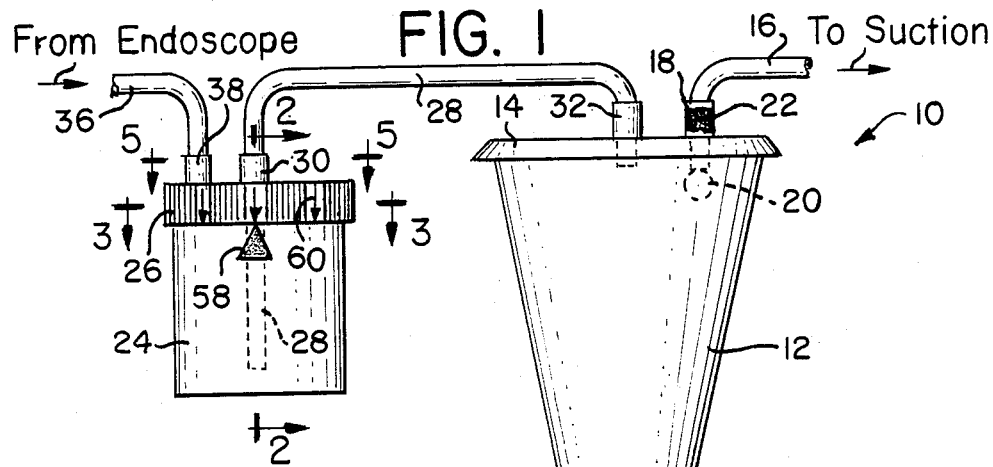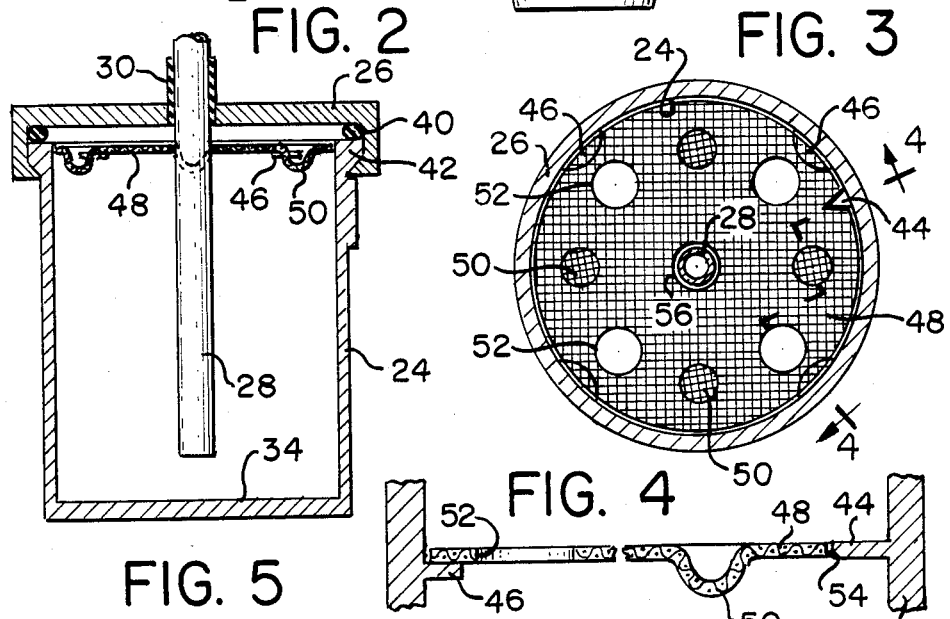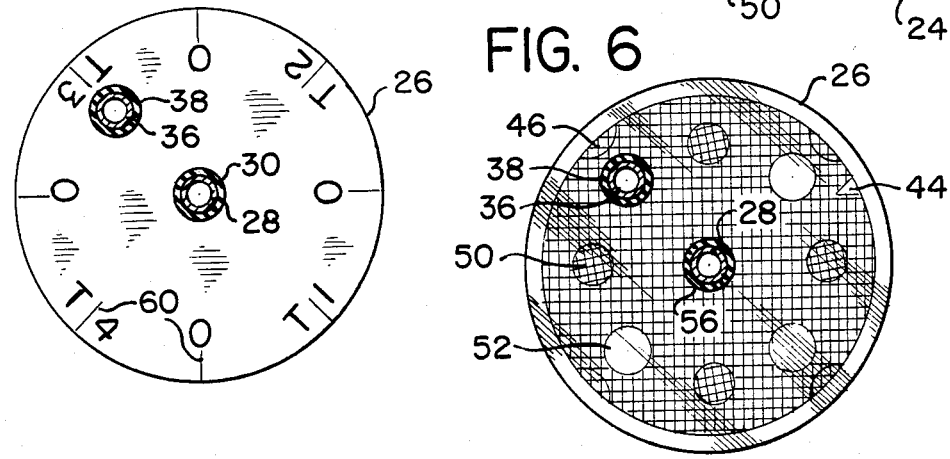

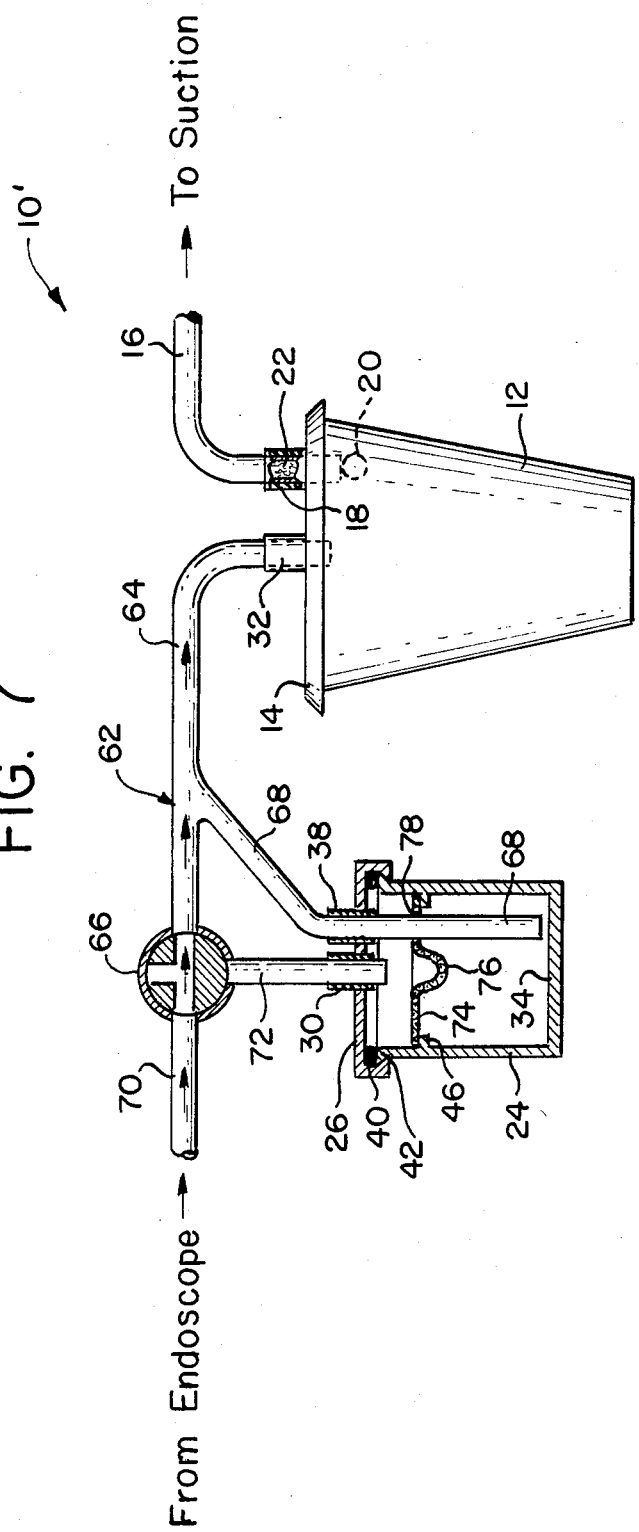
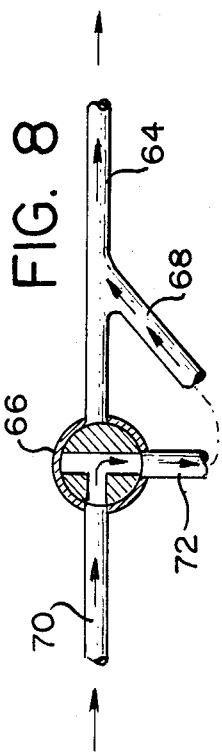

SUCTION COLLECTION AND DRAINAGE APPARATUS

BACKGROUND OF THE INVENTION

This invention is directed generally to a suction collection and drainage apparatus, and more specifically, to a suction trap apparatus for use in collecting body fluids and tissue specimens from a patient.

Heretofore, the medical profession has had available certain suction collection and drainage apparatus in which a collection canister is connected to a source of suction to stimulate drainage from the body of a patient. In some instances, such as shown in U.S. Pat. Nos. 3,704,709 and 3,863,634, the body fluid is collected in a disposable liner positioned within the canister. The apparatus often is used together with a diagnostic instrument, such as an endoscope, to examine body cavities. Typically, the endoscope accomodates a bioptic instrument whereby tissue specimens may be extracted, under suction, from the body cavity and carried through the endoscope into the collection canister. However, it is troublesome and messy to remove the tissue specimen from the filled canister, and/or separate the desired specimen from other debris or tissue aspirated into the same canister.

It also is known to utilize a tissue specimen filter trap positioned in the suction line between the endoscope and the collection canister. While this permits the tissue specimen to be separated from the body fluid, it is necessary to shut down the apparatus and disassemble the suction line to gain access to the specimen once it is collected. This procedure is time consuming in that it must be repeated over and over again when several tissue specimens are to be collected during the same diagnostic examination.

The present invention provides a novel suction collection and drainage apparatus which overcomes the disadvantages associated with the heretofore known systems.

SUMMARY

The suction collection and drainage apparatus of this invention comprises a fluid collection container and a separate tissue specimen trap container. The collection container is connected, by means of a tube, to a source of suction. Another tube serves to connect the collection container and the trap container together to provide fluid communication therebetween. Still another tube serves to connect the trap container to an endoscope to permit collection of tissue specimens aspirated from the patient and transmitted to the trap container.

A filter is supported within the trap container and is formed having a plurality of traps and a plurality of enlarged openings spaced around the filter. The filter is movable relative to the inlet of the tube between a first position wherein a selected one of the traps is positioned to receive and collect the tissue specimen and a second position wherein a selected one of the openings is positioned to permit passage therethrough of body fluids when suction is applied to the apparatus.

In another embodiment of the invention, a valve is associated with the tubing of the apparatus and is operable to selectively cause the body fluid to flow in a path from the patient directly to the collection container bypassing the filter trap container.

For a better understanding of the invention and its various features and advantages, reference should be made to the following detailed description when taken in conjunction with the accompanying drawings.

BRIEF DESCRIPTION OF THE DRAWINGS

FIG. 1 is a side elevational view of the suction collection and drainage apparatus embodying the present invention;

FIG. 2 is a cross-sectional view taken along line 2—2 of FIG. 1;

FIG. 3 is a cross-sectional view taken along line 3—3 of FIG. 1;

FIG. 4 is a cross-sectional view taken along line 4—4 of FIG. 3;

FIG. 5 is a cross-sectional view taken along line 5—5 of FIG. 1;

FIG. 6 is a view similar to FIG. 5 showing another embodiment of the cover associated with the filter trap container;

FIG. 7 is a side elevational view of another embodiment of the invention in which the fluid flow bypasses a modified filter trap container; and FIG. 8 is a partial flow diagram of the apparatus of FIG. 7 showing fluid flow in a path through the filter trap container and then to the collection container.

DESCRIPTION OF THE PREFERRED EMBODIMENTS

Referring to the drawings, particularly FIGS. 1-5, there is shown a suction collection and drainage apparatus 10 constructed in accordance with the present invention. Apparatus 10 includes a fluid collection container 12 provided with a snap-on cover 14. Container 12 is made of plastic and is intended to be disposable.

A tube 16 has one end extending through a suitable fitting 18 on cover 14 to provide communication with the interior of container 12. The inserted end of tube 16 is positioned so as to be located adjacent the top portion of container 12 when cover 14 is in place. The other end of tube 16 is connected to a source of suction.

In order to prevent overflow of container 12, a float valve 20 is associated with the inserted end of tube 16. Valve 20 is operative when the collected body fluid reaches a predetermined level to cut-off the vacuum and stop further fluid flow into container 12. Fitting 18 houses absorbent material 22 to prevent passage of collected body fluid to the source of suction. The absorbent material also may be positioned in a portion of tube 16 between cover 14 and the source of vacuum.

Apparatus 10 further includes a separate second plastic container 24 for collecting tissue specimens. Container 24 is provided with a snap-on cover 26. The coupling of cover 26 to container 24 is such that they are connected together for rotational movement relative to each other. For reasons that will be hereinafter apparent, container 24 is designated as a tissue specimen trap container.

A second tube 28 connects container 24 to container 12 to provide fluid communication between said containers. For this purpose, one end of tube 28 extends through a suitable fitting 30 on cover 26 and the opposite end of tube 28 entends through a fitting 32 on cover 14. Fittings 30 and 32 are positioned such that the ends of tube 28 pass through openings centrally provided in the respective covers 26 and 14. As shown in FIG. 2, the inserted end of tube 28 extends far into container 24 terminating short of the bottom wall 34.

A third tube 36 serves to connect container 24 to an endoscope. More specifically, the inlet end of tube 36 extends through another fitting 38 on cover 26 to permit the collection of tissue specimens within container 24 in a manner hereinafter described.

A sealing ring 40 is provided within cover 26. Ring 40 is adapted to engage with the rim 42 of container 24 to provide a substantially airtight connection between container 24 and its associated cover.

Referring to FIGS. 3 and 4, a tab 44 is provided which projects radially inwardly from the wall of container 24. Positioned around the container wall and spaced slightly below tab 44 are a plurality of support edges 46 which also project radially inwardly from the wall of said container. Tab 44 and ledges 46 cooperate with a filter member 48 to support the filter within container 24 in a manner hereinafter described.

In accordance with the teachings of the invention, filter 48 is a mesh construction and is formed having a plurality of traps 50 and a plurality of openings 52 spaced around the filter. In the embodiment shown in FIG. 3, there are four traps 50 and four openings 52 arranged in an alternating pattern, with the centers of said traps and openings located equidistant from the center of filter 48. It will be apparent that only traps 50 need be of mesh construction, and that the filter 48 itself, aside from openings 52, may be of solid material.

In assembly, filter 48 is inserted within container 24 and supported on ledges 46 which function as a seat for the filter. In order to insure proper orientation and alignment, an edge of filter 48 is provided with a cutout recess portion 54 shaped to receive the projecting tab 44. A central opening 56 is provided in filter 48 through which passes the inlet end of tube 28. As is apparent, the central filter opening 56 is in alignment with the central cover opening to permit insertion of tube 28 through said aligned openings.

In use, the location of filter traps 50 and filter openings 52 is such that rotational movement of filter 48 relative to cover 26 serves to position a selected one of the traps 50 in alignment with the inlet end of tube 36 to receive and collect tissue specimen therein when suction is applied to the apparatus. After collection of the specimen, the filter may again be rotated to position a selected one of the filter openings 52 beneath inlet tube 36 to permit passage therethrough of body fluids. The body fluids are transferred from container 24 to container 12 via tube 28 under suction.

In accordance with the present embodiment, since filter 48 is keyed to container 24 for rotation therewith, the rotation of filter 48 relative to cover 26 is achieved simply by rotating the container relative to its cover. Alternatively, the container can be held stationary and the cover rotated relative thereto. Still further, it is conceivable that the filter 48 may be supported by the cover 26 in a position spaced below the inlet end of tube 36. In such event, both the container 24 and its associated cover 26 may be held stationary, and the filter 48 selectively rotated by suitable linkage in a lazy Suzan fashion, as desired.

In order to assure that filter 48 is in a proper position to locate either a trap 50 or an opening 52 beneath the inserted end of tube 36, indicating means are provided in the form of a pointer 58 vertically positioned on the outer wall of container 24. As shown in FIGS. 1 and 5, pointer 58 cooperates with a plurality of indicia markings 60 on cover 26 to indicate the position of container 24 relative to its associated cover. Specifically, the markings 60 appear on the top and side wall of cover 26 and serve to identify particular ones of the traps 50 and openings 52. For example, the markings for the four traps 50 are T/1, T/2, T/3 and T/4. The marking for the openings 52 is the letter "O". It thus will be appreciated that the alignment of pointer 58 with a selected cover marking 60 upon movement of container 24 relative to its associated cover 26 serves to indicate which one of the traps 50 or openings 52 identified by its marking is positioned in alignment with tube 36.

In place of the aforesaid pointer and markings, snap engaging cooperative elements may be provided on container 24 and cover 26, which elements are disposed to engage upon rotation of the container and associated cover relative to each other to locate either a trap 50 or an opening 52 beneath tube 36. Still further, the cover 26 may be transparent, as shown in FIG. 6, so as to visually observe the orientation of filter 48 relative to tube 36. For example, the orientation of filter 48 in FIG. 6 is such as to locate one of the openings 52 beneath tube 36.

There is thus disclosed a novel collection and drainage apparatus wherein up to four separate tissue specimens can be collected without having to shut down the system. The specimens are easily retrieved by removing cover 26 to gain access to filter 48. If desired, the tubing 28 and 36 may be pulled free from cover 26, and the trap container filled with formaldehyde solution. This would act as a preservative until the trap container reaches the pathologist's lab.

FIGS. 7 and 8 illustrate another embodiment of the invention, represented by apparatus $10^1$ wherein those parts common to the embodiment of FIG. 1 are identified by the same reference numbers. For this embodiment, the tube which serves to connect collection container 12 to the filter trap container 24 is identified generally by numeral 62. Tube 62 comprises a segment 64 having one end which passes through fitting 32 on cover 14 to provide fluid communication with the interior of container 12. The opposite end of tube segment 64 connects to a three-way valve 66. Between the ends of tube segment 64, there is provided a branch or second tube segment 68 which passes through the fitting 38 on cover 26 and terminates spaced slightly away from the bottom wall 34 of filter trap container 24. As is now apparent, tube segments 64 and 68 provide fluid communication between containers 12 and 24.

Another tube 70 serves to connect the endoscope to valve 66, and still another tube 72 serves to connect container 24 to valve 66. As shown in FIG. 7, the inlet end of tube 72 extends through the central fitting 30 on cover 26 of container 24.

Supported within container 24 on ledges 46 is a filter 74 constructed having a central trap 76 which is located spaced below the inlet end of tube 72. Filter 74 also has an opening 78 located and sized to permit passage therethrough of the lower portion of tube segment 68.

In operation, valve 66 may be positioned, as shown in FIG. 7, to cause body fluid to flow in a path from the patient to collection container 12, via tubes 70 and 64, bypassing filter trap container 24, when suction is applied to the apparatus. At such time as a tissue specimen is to be collected, valve 66 is turned to the position shown in FIG. 8 whereby the flow path is directed to container 24 via tubes 70 and 72, and then to container 12 via tubes 68 and 64.

A feature of this embodiment is that the system need not be shut down to gain access to filter 74. As is apparent, fluid flow may be directed from the endoscope directly to collection container 12 thereby permitting filter trap container 24 to be removed from the system and taken to the pathologist's lab.

It further is apparent that the connection of tube segment 68 to container 24 can be through the bottom wall 34 of said container to obtain substantially full drainage of fluid from the container.

While the present invention has been described with respect to particular embodiments, it will be readily appreciated and understood that numerous variations and modifications thereof may be made without departing from the spirit or scope of the claimed invention.

We claim:

1. A suction collection and discharge apparatus for use in collecting body fluids and tissue specimens from a patient, said apparatus comprising:
    a first container for receiving and collecting body fluids, said container having a cover;
    a first tube having one end extending through said cover and communicating with the interior of said first container, the other end of said tube adapted to be connected to a source of suction;
    a second container for collecting tissue specimens, said second container having a cover;
    a second tube connecting said second container to said first container to provide fluid communication between said first and second containers, said second tube adapted to receive and permit passage therethrough of body fluids;
    a third tube having one end extending through the cover of said second container and communicating with the interior of said second container, the other end of said third tube adapted to receive and permit passage therethrough of body fluids and tissue specimens; and
    a filter supported within said second container, said filter having a plurality of traps and a plurality of enlarged openings spaced around said filter;
    said second container and its associated cover being movable relative to each other between a first position wherein a selected one of said traps is positioned to receive and collect the tissue specimen and a second position wherein a selected one of said openings is positioned to permit passage therethrough of body fluids when suction is applied to said apparatus.

2. The apparatus of claim 1, wherein said plurality of traps and openings are spaced around the filter in an alternating pattern.

3. The apparatus of claim 1, further comprising locating means on said second container, said locating means being engageable with said filter to permit proper insertion of said filter within said container.

4. The apparatus of claim 3, wherein said locating means comprises a tab projecting radially inwardly from the wall of said second container and a mating recess formed in said filter, said recess adapted to receive said tab when said filter is supported within said container.

5. The apparatus of claim 1, wherein said second container and its associated cover are connected together for rotational movement relative to each other, and said apparatus further comprising indicating means on said second container and associated cover to indicate the position of said container relative to its cover.

6. The apparatus of claim 5, wherein said indicating means comprises a pointer on said second container and a plurality of markings on the associated cover, said cover markings identifying particular ones of said plurality of traps and openings, whereby the alignment of said pointer with a selected cover marking upon movement of said container and associated cover relative to each other serves to indicate which one of said traps or openings identified by said marking is positioned in alignment with said one end of said third tube.

7. The apparatus of claim 1, further comprising supporting means within said second container, said filter adapted to engage said supporting means and be supported thereon.

8. The apparatus of claim 7, wherein said supporting means comprises a ledge projecting radially inwardly from the wall of said second container, said ledge serving as a seat for said filter.

9. The apparatus of claim 1, wherein the cover associated with said second container has an opening, said filter having an opening aligned with the opening in said cover, one end of said second tube passing through the aligned openings in said cover and said filter, and the other end of said second tube extending through the cover of said first container.

10. The apparatus of claim 9, wherein the aligned openings of said cover and said filter through which said second tube passes are centrally located in said cover and said filter.

11. The apparatus of claim 1, wherein the centers of said plurality of traps and openings are equidistant from the center of said filter.

12. The apparatus of claim 1, further comprising a sealing ring in the cover of said second container, said sealing ring adapted to engage with said container to provide a substantially airtight connection between said container and its associated cover.

13. The apparatus of claim 1, further comprising a valve located within said first container and associated with said first tube, said valve being operative when the collected body fluid reaches a predetermined level to cut-off the vacuum and stop further fluid flow into said first container.

14. The apparatus of claim 1, further comprising absorbent means in said first tube to prevent passage of body fluid to the source of suction.

15. The apparatus of claim 1, wherein the cover associated with said second container is transparent.

16. The apparatus of claim 1, further comprising a valve associated with said second tube and said third tube, said valve being operative to selectively cause the body fluid to flow in a path from the patient to said first container bypassing said second container.

17. A suction collection and drainage apparatus for use in collecting body fluids and tissue specimens from a patient, said apparatus comprising:
    a first container for receiving and collecting body fluids, said container having a cover;
    a first tube having one end extending through said cover and communicating with the interior of said first container, the other end of said tube adapted to be connected to a source of suction;
    a second container for collecting tissue specimens, said second container having a cover;
    a second tube connecting said second container to said first container to provide fluid communication between said first and second containers, said second tube adapted to receive and permit passage therethrough of body fluids;

a third tube having one end extending through the cover of said second container and communicating with the interior of said second container, the other end of said third tube adapted to receive and permit passage therethrough of body fluids and tissue specimens; and entrapment means associated with said second container, said entrapment means comprising a filter supported within said second container, said filter having a plurality of traps;

said second container and its associated cover being movable relative to each other to locate a selected one of said traps in a position to receive and collect the tissue specimen when suction is applied to said apparatus.

18. The apparatus of claim 17, wherein said selected trap is positioned below and in alignment with said one end of said third tube.

19. A suction collection and drainage apparatus for use in collecting body fluids and tissue specimens from a patient, said apparatus comprising:

a first container for receiving and collecting body fluids, said container having a cover;

a first tube having one end extending through said cover and communicating with the interior of said first container, the other end of said tube adapted to be connected to a source of suction;

a second container for collecting tissue specimens, said second container having a cover;

a second tube connecting said second container to said first container to provide fluid communication between said first and second containers, said second tube adapted to receive and permit passage therethrough of body fluids;

a third tube having one end extending through the cover of said second container and communicating with the interior of said second container, the other end of said third tube adapted to receive and permit passage therethrough of body fluids and tissue specimens; and entrapment means associated with said second container, said entrapment means comprising a filter supported within said second container, said filter having a trap and an enlarged opening;

said filter being movable relative to the cover of said second container between a first position wherein said trap is positioned to receive and collect the tissue specimen and a second position wherein said opening is positioned to permit passage therethrough of body fluids when suction is applied to said apparatus.

20. A suction collection and drainage apparatus for use in collecting body fluids and tissue specimens from a patient, said apparatus comprising:

a first container for receiving and collecting body fluids, said container having a cover;

a first tube having one end extending through said cover and communicating with the interior of said first container, the other end of said tube adapted to be connected to a source of suction;

a second container for collecting tissue specimens, said second container having a cover;

a second tube connecting said second container to said first container to provide fluid communication between said first and second containers, said second tube adapted to receive and permit passage therethrough of body fluids;

a third tube having one end extending through the cover of said second container and communicating with the interior of said second container, the other end of said third tube adapted to receive and permit passage therethrough of body fluids and tissue specimens; and entrapment means associated with said second container, said entrapment means comprising a filter supported within said second container, said filter having a trap and an enlarged opening;

said second container and its associated cover being movable relative to each other between a first position wherein said trap is positioned to receive and collect the tissue specimen and a second position wherein said opening is positioned to permit passage therethrough of body fluids when suction is applied to said apparatus.

* * * * *